United States Patent [19]

Pesa et al.

[11] Patent Number: 4,510,320

[45] Date of Patent: Apr. 9, 1985

[54] PREPARATION OF ALIPHATIC CARBOXYLIC ACID ESTERS

[75] Inventors: Frederick A. Pesa, Aurora; Anne M. Graham, Northfield, both of Ohio

[73] Assignee: The Standard Oil Co. (Ohio), Cleveland, Ohio

[21] Appl. No.: 334,484

[22] Filed: Dec. 24, 1981

[51] Int. Cl.³ .................. C07C 1/06; C07C 1/253; C07C 9/04; C07C 9/06; C07C 9/08; C07C 67/36; C07C 69/14

[52] U.S. Cl. .................. 560/265; 502/178; 502/243; 502/326; 502/327; 518/717; 562/607; 568/387; 585/639; 585/733

[58] Field of Search ............. 560/265, 232; 585/733; 518/717; 252/473, 474; 502/326, 327

[56] References Cited

U.S. PATENT DOCUMENTS 2,965,660  2/1960  Heise et al. .............. 560/265
4,077,912  3/1978  Dolhyj et al. ............ 252/461
4,270,015  5/1981  Knifton ................... 585/324

Primary Examiner—Vivian Garner
Attorney, Agent, or Firm—J. G. Curatolo; L. W. Evans

[57] ABSTRACT

A process is provided for the production of aliphatic acetate esters and gaseous alkanes comprising contacting acetic acid and synthesis gas in the vapor phase at elevated temperature and pressure in the presence of a catalyst containing the mixed oxides of ruthenium and nickel, and optionally an alkali metal oxide and the oxides of cobalt, cadmium, zinc or mixtures thereof. Other carboxylic acids may be substituted for acetic acid as desired.

8 Claims, No Drawings 4,510,320

PREPARATION OF ALIPHATIC CARBOXYLIC ACID ESTERS

BACKGROUND OF THE INVENTION

The present invention is directed to a process for producing carboxylic acid esters. More particularly, the present invention includes a process for the preparation of aliphatic esters of acetic acid from acetic acid and synthesis gas.

Carboxylic acid esters are generally produced by contacting a carboxylic acid with an alcohol in the presence of a catalyst.

U.S. Pat. No. 4,270,015, discloses the preparation of the ethyl ester of acyclic carboxylic acids by contacting the carboxylic acid with synthesis gas in the liquid phase in the presence of a Group VA ligand promoted ruthenium catalyst.

We have found that carboxylic acid esters can be produced in the vapor phase by contacting the carboxylic acid with synthesis gas in the presence of a mixed oxide catalyst containing ruthenium and nickel.

SUMMARY OF THE INVENTION

The process of the present invention includes the preparation of carboxylic acid esters such as the aliphatic esters of acetic acid containing up to 12 carbon atoms and low molecular weight alkanes such as methane, ethane and propane by contacting a carboxylic acid with synthesis gas ($CO+H_2$) in the vapor phase in the presence of a catalyst containing the mixed oxides of ruthenium and nickel.

DETAILED DESCRIPTION OF THE INVENTION

In the process of the present invention, preferably acetic acid is contacted with synthesis gas at elevated temperature and pressure in the presence of a catalyst containing the mixed oxides of ruthenium and nickel. Other acids, such as propanoic acid may be utilized also.

Synthesis gas may be produced by means known in the art and practiced commercially, including providing synthesis gas as a product of the partial combustion of coal, natural gas, petroleum bottoms or other carbonaceous materials. One method of derivation is heating of coke in the presence of air and then steam. The ratio of carbon monoxide to hydrogen in the synthesis gas mixture may vary from about 0.1:1 to about 10:1 and is preferably in the range of about 1:3 to about 3:1. The synthesis gas may contain a very low amount of sulfur compounds, and may also contain small amounts of carbon dioxide, nitrogen and other inerts. Although synthesis gas is a preferred reactant, any other gas composed primarily of hydrogen and carbon monoxide and having a $CO:H_2$ ratio of about 0.1:1 to about 10:1 may be employed. Preferably the gaseous reactant is essentially sulfur-free.

Process Conditions

The process of the present invention is carried out by contacting the carboxylic acid, carbon monoxide and hydrogen with the catalyst described below in a suitable fluid-bed or fixed-bed reactor. The reaction can be conducted continuously or in a batch type operation. It should be noted that the reaction takes place in the vapor phase. The reaction temperature should be maintained between about 250° C. to about 400° C., preferably about 275° C. to 375° C.

The reaction pressure should normally be about 250 psi to about 5000 psi, preferably about 500 psi to about 1500 psi. The reactant gases may be fed to the reactor utilized at a space velocity (liters gaseous reactant/liters of catalyst/hour) of about 100/hr. to about 10,000/hr., preferably about 500/hr. to 5,000/hr.

The contact time of the reactants with the catalyst is generally between about 10 seconds to about 200 seconds, and is preferably about 40 seconds to about 140 seconds.

Catalyst

The catalyst utilized in the process of the present invention comprises the mixed oxides of ruthenium and nickel, preferably containing an alkali metal selected from Na, Li, K, Rb and Cs, although Na is preferred. The molar ratio of ruthenium to nickel is generally about 0.1:1 to about 10:1, preferably about 0.3:1 to 3:1. The molar ratio of alkali metal, if present, to ruthenium is generally about 0.01:1 to about 0.5:1.

The catalyst optionally may include promoter metal oxides including Zn, Cd, Co and mixtures thereof, in a molar ratio to ruthenium of about 0.01:1 to about 1:1.

The catalyst of the present invention is a mixed metal oxide. In the process of the present invention, the catalyst is preferably utilized in a partially reduced state, however, the catalyst is not totally reduced to the metallic state and thus retains its oxide character.

The catalyst may be prepared by conventional means, such as by mixing compounds containing the catalyst components in a liquid solution or slurry, such as a water solution or slurry and heating, recovering the catalyst precursor from the liquid, drying and calcining. Catalyst component-containing compounds may include but are not limited to oxides, hydroxides, inorganic salts such as nitrates, phosphates, halides, carbonates, silicates, aluminates and salts of organic acids such as acetates, formates, butyrates, propionates, benzylates, and the like. The catalyst may be formed in a conventional manner, such as tableting, pelleting or supporting the active catalyst material on a carrier. The carrier is preferably inert, and may include silica, alumina, Alundum, clay, alumina-silica, silicon carbide and the like. The active catalytic material may be coated on the carrier by the method described in U.S. Pat. No. 4,077,912 or may be impregnated on the carrier such as by depositing a solution of the catalyst component-containing compounds onto a carrier, drying and calcining.

Products

Products of the process of the present invention include the aliphatic esters of the carboxylic acid. When acetic acid is utilized as a reactant, the products include the $C_3$ to $C_{12}$ aliphatic esters of acetic acid, including methyl acetate, ethyl acetate, propyl acetate and the like. These products are useful as solvents, liquid transportation fuels and chemical intermediates. For example, ethyl acetate can be pyrolized to yield ethylene, a basic chemical feed stock, and acetic acid, yielding the net reaction of carbon monoxide plus hydrogen resulting in ethylene.

By-products of the process of the present invention include synthesis gas upgrading products such as methane, ethane, propane and the like, all of which are useful as fuels.

EXAMPLE 1

A catalyst of the formula 5% $RuNiNa_{0.1}O_x$ (where x is the number of oxygen atoms needed to satisfy the valence requirements of the other elements), 95% Alundum (alumina-silica) was prepared by the following method:

An amount of ruthenium chloride and nickel chloride required to give 0.03 moles of each metal was dissolved in 250 ml of water with stirring for 30 minutes. Aqueous sodium hydroxide (50% by weight) was added dropwise, with stirring until the pH reached and remained at 8.3 to 8.5. The resulting slurry was heated near boiling for 30 minutes with constant stirring, then cooled. The pH was adjusted to 7.5. The mixture was filtered, washed and reslurried with subsequent filtering and washing steps until the molar ratio of sodium to ruthenium present was approximately 0.1:1. The solid mixed oxide was dried at 125° C. for about 16 hours, was calcined for 3 hours at about 350° C. in air and was ground to pass 140 mesh (0.105 mm).

The catalyst was coated upon an alumina-silica support in the following manner: 25 gm of Norton -SA 5223 Alundum, 10/30 mesh (0.595 mm–2.00 mm) were placed in a vessel. 1.25 gm distilled water was sprayed onto the Alundum which was rolled for approximately 10 minutes and the procedure was repeated. The metal oxide catalyst, in an amount calculated to give the total of 0.015 moles of active metal, was added in two equal portions with 15 minutes rolling after each. The coated catalysts was dried for about 16 hours at 125° C. and calcined 3 hours at 350° C.

The catalyst was partially reduced in the following manner:

A 20 cc stainless steel tube reactor was packed with catalyst, and hydrogen gas was introduced into the reactor at 150-200 cc/min. at atmospheric pressure. The electric block furnace placed around the reactor was increase in 50° increments step wise until 500° C. was reached. The final temperature was maintained for 2 hours, at which time the reactor was allowed to cool with hydrogen flow being continued.

EXAMPLE 2 (COMPARATIVE)

A catalyst of the formula 5% $RuFeNa_{0.1}O_x$ was prepared by the procedure of Example 1 except that $FeCl_3$ was substituted for nickel chloride.

Reaction Procedure

Following catalyst reduction and subsequent cooling to room temperature, the reactor was charged to the desired pressure with hydrogen. The furnace surrounding the reactor was activated and set for run temperature. The system was allowed to equilibrate for at least 15 minutes at run temperature before carbon monoxide flow started and both gases were adjusted to the desired flow rates. Acetic acid was fed to the reactor at 6-12 ml/hour, being fed to the reactor as a vapor. In Example 1, the reaction was conducted at a temperature of 375° C., a pressure of 600 psi, CO:H$_2$ ratio of 1:1, space velociry of 510/hour. 61.2% of the CO was converted to either product or waste (CO$_2$) Selectivity to methane was 57% and 6.1% to ethane and propane.

$$\text{Selectivity} = \frac{\text{moles of product formed}}{\text{moles CO input} - \text{moles CO effluent}} \times 100$$

Aliphatic acetate esters were formed, including the methyl, ethyl, and propyl acetates, and higher acetate esters containing up to 12 carbon atoms, at a selectivity of about 20% for all esters., Methyl, ethyl and propyl esters predominated.

In Example 2 (Comparative), run temperature was 300° C., pressure was 300 psi, CO:H$_2$ ratio was 1:1, and the space velocity was 510/hour. CO conversion was only 37%, and besides 20% methane and 7.1% higher gaseous alkanes, acetone was produced. No aliphatic acetate esters were detected.

Thus it should be apparent to those skilled in the art that the subject invention accomplishes the object set forth above. It is to be understood that the subject invention is not to be limited by the example set forth herein. This has been provided merely to demonstrate operability and the selection of catalyst component-containing compounds, catalyst formulations, synthesis gas component ratios, carboxylic acid, and reaction conditions can be determined from the total specification disclosure provided without departing from the spirit of the invention herein disclosed and described, the scope of the invention including equivalent embodiments, modifications and variations which fall within the scope of the attached claims.

We claim:

1. A process for the production of aliphatic acetate esters containing up to 12 carbon atoms and gaseous alkanes comprising contacting acetic acid, carbon monoxide and hydrogen in the vapor phase at a temperature of about 250° C. to about 400° C. and a pressure of about 250 psi to about 5,000 psi in the presence of a catalyst containing the mixed oxides of ruthenium, nickel, an alkali metal selected from Na, Li, K, Rb and Cs, and optionally a promoter metal selected from cobalt, cadmium, zinc, or mixtures thereof.

2. A process as in claim 1 wherein the molar ratio of ruthenium to nickel is between about 0.1:1 to about 10:1.

3. A process as in claim 1 wherein said catalyst contains said alkali metal oxide in a molar ratio to ruthenium of about 0.01 to about 0.5.

4. A process as in claim 3 wherein said alkali metal is sodium.

5. A process as in claim 4 wherein the molar ratio of ruthenium:nickel equals 1:1.

6. A process as in claim 1 or 3 wherein said catalyst additionally contains an oxide of cobalt, cadmium, zinc or mixtures thereof in a molar ratio to ruthenium of about 0.01:1 to about 1:1.

7. A process as in claim 1 wherein said catalyst is supported on an inert carrier.

8. A process as in claim 7 wherein said carrier is selected from alumina, silica, alumina-silica, clay and silicon carbide.

* * * * *